United States Patent [19]

Sakoda et al.

[11] Patent Number: 5,711,862
[45] Date of Patent: Jan. 27, 1998

[54] PORTABLE BIOCHEMICAL MEASUREMENT DEVICE USING AN ENZYME SENSOR

[75] Inventors: Yusaku Sakoda; Hideki Endo; Satoshi Nakajima, all of Kyoto, Japan

[73] Assignee: OMRON Corporation, Kyoto-fu, Japan

[21] Appl. No.: 616,399

[22] Filed: Mar. 15, 1996

[30] Foreign Application Priority Data

Mar. 15, 1995 [JP] Japan .................................. 7-054834

[51] Int. Cl.⁶ .................................................. G01N 27/26
[52] U.S. Cl. ...................................... 204/403; 435/817
[58] Field of Search .................................. 204/403, 415, 204/406, 407; 435/817

[56] References Cited

U.S. PATENT DOCUMENTS

| | | | |
|---|---|---|---|
| 4,923,586 | 5/1990 | Katayama et al. | 204/403 |
| 4,933,066 | 6/1990 | Osaka et al. | 204/403 |
| 5,589,045 | 12/1996 | Hyodo | 204/403 |

*Primary Examiner*—Bruce F. Bell
*Attorney, Agent, or Firm*—Morrison & Foerster LLP

[57] ABSTRACT

A portable biochemical measurement device including a measurement main body containing an enzyme sensor holder for an enzyme sensor. A cover, mounted on the measurement main body, covers the enzyme sensor holder. The cover contains a chamber filled with a liquid medium to maintain the moisture of the enzyme sensor. Inside the cover are a cartridge and packing, which form the chamber containing the liquid medium. The enzyme sensor holder is inserted into the cover through the packing so that the enzyme sensor is immersed in the liquid medium thereby keeping the enzyme sensor moist.

12 Claims, 5 Drawing Sheets

PORTABLE BIOCHEMICAL MEASUREMENT DEVICE USING AN ENZYME SENSOR

FIELD OF THE INVENTION

This invention relates to a portable biochemical measurement device for biochemical applications which employs an immobilized enzyme sensor.

BACKGROUND OF THE INVENTION

In clinical research, enzymes are used in the identification and quantitative analysis of a specific substance in a sample of a compound. The following two methods are the ones most frequently employed. One is to combine the enzyme with a chromatic reagent so that the degree of reaction to the enzyme is converted to a color variation. Upon detecting this variation optically, the quantity of the specified substance (or substrate) can be measured. The other method is to expose the enzyme to an electrode and detect electrochemically the substance which varies with the reaction. From this electrical variation the quantity of the specified substance (or substrate) can be measured.

With the latter method, the enzyme is sometimes mixed and combined with a sample solution, however, this requires the use of large equipment. For most applications, the enzyme is immobilized, formed into a thin film and exposed to an electrode, thereby allowing smaller equipment to be used. However, with small equipment it is difficult to keep constant the contact of the electrode to the immobilized enzyme film.

By maintaining at a constant rate the diffusion of the target substance (or substrate) in the liquid sample to be tested onto the immobilized enzyme layer and the diffusion of a substance which is a product of the enzyme reaction onto the electrode surface, a stable measurement result can be achieved. Conversely, if the contact of the electrode to the enzyme film or a moisture level between the electrode and the film is allowed to vary, the measurement result will vary.

Attempts have been made to enhance efficiency by using a jig to maintain constant contact of the electrode to the enzyme film at the time the film is attached. However, because the user must change jigs throughout the process, there is no way to avoid unstable contact due to defective installation by a jig.

One way to maintain a constant moisture for the immobilized enzyme sensor is to place the sensor in a flow cell to which the sample and the liquid medium are supplied. Unless a flow cell is used, a pump is required for this purpose. No matter what method is chosen, substantial equipment is needed to maintain the supply of the liquid medium and to keep the compartment watertight, thereby driving up cost. Also, either a specified quantity of the sample must be supplied to the sensor or the sample must be collected in a container with the sensor immersed in it.

Recently, methods have been proposed which address some of these problems. In one such method the moisture level of the enzyme sensor is maintained by infusing the liquid medium into a sponge-like substance with numerous holes. This substance keeps the reactive surface of the immobilized enzyme sensor at a constant moisture level, which results in a smaller, more portable device. However, the device requires another membrane to limit diffusion which must be reinstalled before each measurement, thereby making the ease of operation and stability less than satisfactory. The pressure welds on the electrode and the absorptive layer can easily be altered by the elastic deformation of the absorptive layer, which is made of a soft material. When this happens, the circulation of the liquid medium may be impeded, resulting in a quantity insufficient to contain the sensor. For storage, the device must be completely sealed, making it liable, which is not affected by pressure changes resulting from temperature variation.

SUMMARY OF THE INVENTION

A portable biochemical measurement device comprises a main measurement unit consisting of a measurement circuit, power supply, enzyme sensor holder and a removable cover. The enzyme sensor holder contains an enzyme sensor. The cover contains a chamber filled with a medium to maintain the enzyme sensor's moisture. The medium is contained in a hermetically seal chamber consisting of a cartridge and a packing. The enzyme sensor holder is inserted into the cover through a packing so that the enzyme sensor is immersed into the medium thereby keeping the enzyme sensor moist.

The cover is removed from the measurement device when a measurement is to be made. The sensor holder (along with the enzyme sensor) is now exposed to allow a measurement to be made. Conversely, when the cover is mounted on the measurement device, the enzyme sensor is immersed in the liquid medium inside the cover so as to maintain it in a state of constant moisture.

The cover has two segments, a base and top segments. These two segments can be removed by releasing an engagement formed at the side of the segments. The top segment holds a cartridge and a packing within the segment whereby the cartridge and packing are removable from the top cartridge. In addition, top segment is also removable from the base segment. When the top segment of the cover is engaged with the base segment, the cartridge and packing are fixed in the correct position inside the cover. When the power supply is off, the cartridge can be removed independently from the top segment. This makes it easier to add to or replace the liquid medium or to wash out the cartridge. It is also effective in improving safety by preventing electric discharge of the battery.

The enzyme sensor consists of a hydrogen peroxide electrode formed on an insulated substrate. An immobilized enzyme layer then is formed on this electrode. This arrangement provides an efficient enzyme reaction with respect to the sample to be tested. It also makes it easy to produce a sensor of a shape suited to the intended application.

The enzyme sensor is contained in the enzyme sensor holder together with a protective film or membrane, to protect its surface. This protects the enzyme sensor from external physical shock and thereby extends the sensors service life. The protective film can also filter out buffers which might affect the enzyme reaction, contributing to a stable and reliable measurement.

This protective film is held in place by an O ring in the sensor holder. When the enzyme sensor is fitted into the holder, the protective film is made to adhere firmly to the sensor. This way the moisture level of the film with the sensor is kept constant at all times so that a stable measurement can be made. The use of an O ring also allows the interior of the sensor to be watertight, thus lengthening its service life and contributing to more stable operation. Since the O ring fulfills two functions at once, it allows the enzyme sensor to achieve stable operation despite a simple configuration.

The overall effect of the features discussed above is a small, lightweight, portable, biochemical measurement device which is reliable and easy to operate.

DESCRIPTION OF THE PREFERRED EMBODIMENTS

Figure 1:
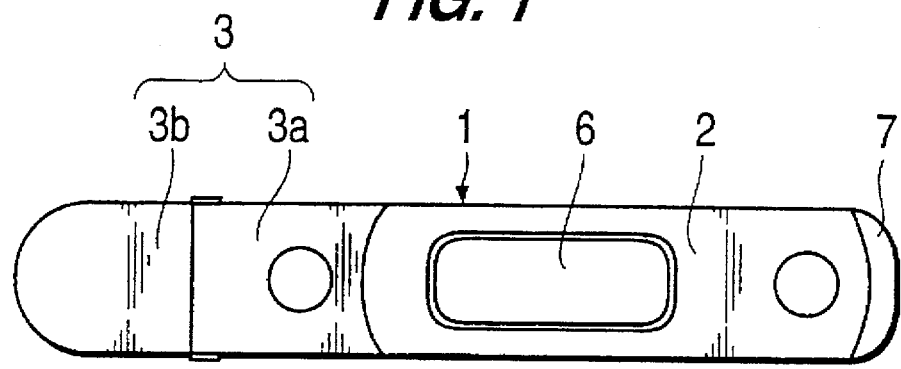
FIG. 1 is an overhead view of a measurement device which is an ideal embodiment of this invention.
Figure 2:
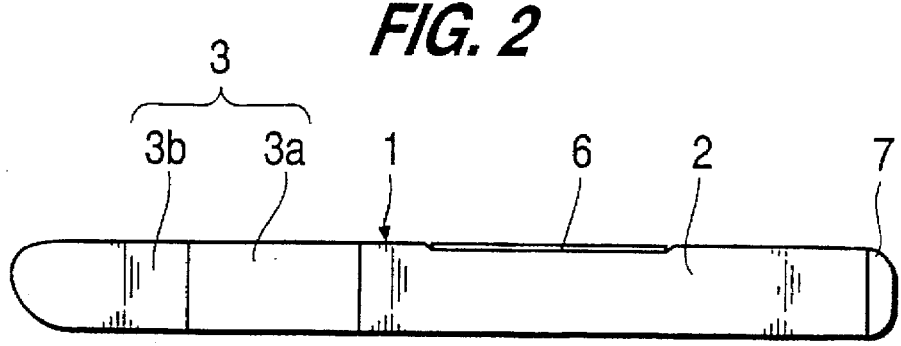
FIG. 2 is a lateral view of the measurement device in FIG. 1.

FIG. 1 shows the top surface of the biochemical measurement device and FIG. 2 shows the device's side view. Measurement device 1 includes a measurement main body 2 which contains a removable cover 3, a display 6, a battery case 7, a measurement circuit and a power supply (not shown). The measurement circuit contains a computing element, a buzzer and various other electronic components (not shown). The cover contains a base segment 3a and a top segment 3b. These two segments can be removed from the device 1 by releasing an engagement formed on the side of the segments.

Figure 3:
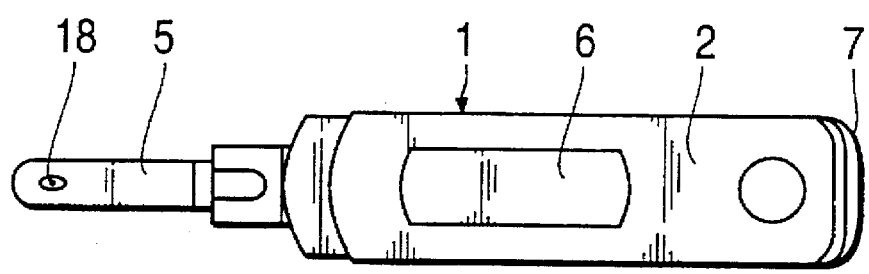
FIG. 3 is an overhead view of the measurement device in FIG. 1 with its cover removed.
Figure 4:
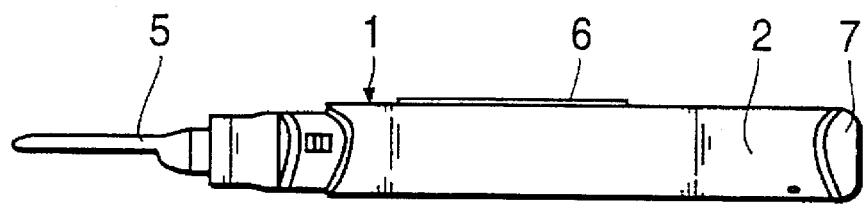
FIG. 4 is a lateral view of the measurement device in FIG. 3.
Figure 5:
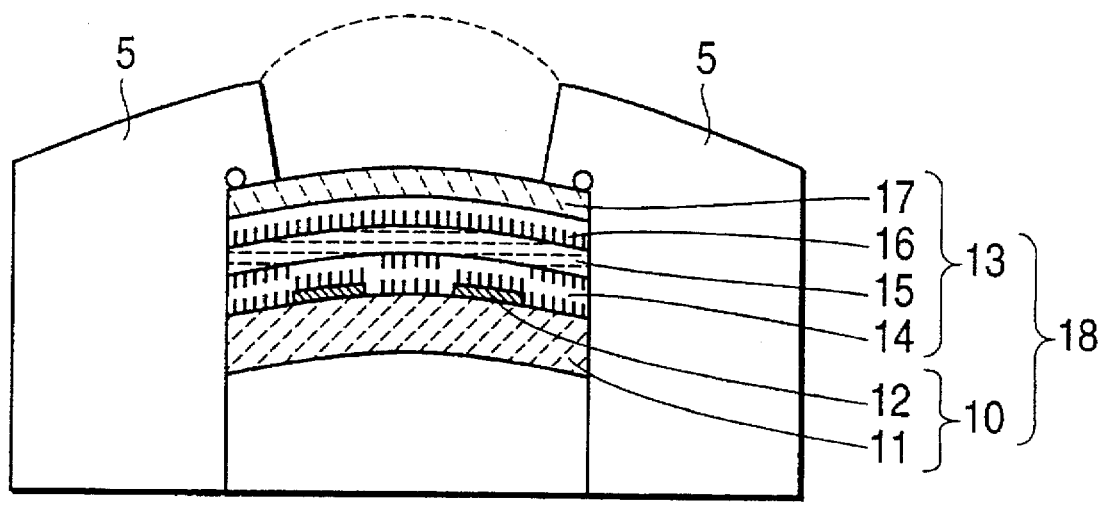
FIG. 5 is a cross section showing the essential components of an enzyme sensor which could be contained in the sensor holder.

In FIGS. 3 and 4, when the cover 3 is removed from the measurement main body 2, an enzyme sensor 18 is contained in an enzyme sensor holder 5. This enzyme sensor 18 within enzyme sensor holder 5 is pictured in FIG. 5. Sensor 18 is composed of a base electrode 10 and an immobilized enzyme films 13. The base electrode 10 is placed on the sensor holder 5 while the immobilized enzyme films 13 is stacked on top of the base electrode 10. The electrode 10 and the enzyme films 13 together form an integral unit.

The following are two possible choices for base electrode 10:

(1) A field effect transistor may be used as an element to convert voltage to current. In this case, an insulated gate is provided on the outermost portion of the transistor, and layers of immobilized enzyme are formed one after another on this portion. The Ph change which accompanies the enzyme reaction is apprehended as a change in the gate voltage (which is simultaneously converted to a change in the drain current); or (2) A generally planar oxygen electrode or hydrogen peroxide electrode may be used as an element to convert current to voltage. In this case, the layers of immobilized enzyme are formed on the reactive surface, and the increase or decrease in oxygen or hydrogen peroxide which accompanies the enzyme reaction is apprehended as a change in the oxidation current of the base electrode. Various metals may be used for the electrode. Common choices would be platinum (Pt) for the active electrode and gold (Au), platinum (Pt) or silver (Ag) for the reference or opposed electrode.

The following four enzymes are examples of enzymes which may be used in enzyme sensor 18:

(1) Glucose Oxidase Enzyme (GOD)

Glucose+$O_2$→Gluconate+$H_2O_2$

This reaction is accompanied by the consumption (i.e., a decrease) of oxygen ($O_2$), the creation (i.e., an increase) of hydrogen peroxide and the creation of gluconate (i.e., a decrease in Ph);

(2) Lactose Oxidase Enzyme (LOD)

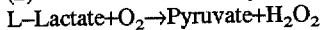

L–Lactate+$O_2$→Pyruvate+$H_2O_2$

This reaction is accompanied by the consumption (decrease) of oxygen ($O_2$) and the creation (increase) of hydrogen peroxide ($H_2O_2$);

(3) Urease

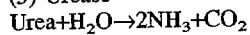

Urea+$H_2O$→$2NH_3$+$CO_2$

This reaction is accompanied by the creation of ammonia (an increase in Ph due to a decrease in the density of hydrogen ions) and an increase in $CO_2$ gas; and (4) Uricase

Urea+$O_2$+$2H_2O$→Allantoin+$H_2O$+$CO_2$

This reaction is accompanied by the consumption (decrease) of oxygen ($O_2$), the creation (increase) of hydrogen peroxide ($H_2O_2$) and an increase in $CO_2$ gas.

Typically, immobilized enzyme film 13 would have an immobilized enzyme film 15 composed of one of the aforesaid enzymes enclosed in a protective sandwich. Immobilized enzyme film 15 is formed either by creating a bridge using a bridge-building material with a sensitive base or by surrounding the enzyme with a gel lattice or a macromolecule.

Lower protective film 14 limits the permeation of the intervening material to the electrode surface as needed. Base electrode 10 and immobilized enzyme film 15 must remain in contact and remain stable. For this purpose acetyl cellulose or an ion exchange film may be used. Upper protective film 16 serves to protect immobilized enzyme film 15 and restrict the diffusion of the substrate to the immobilized enzyme film 15. Therefore, upper protective film 16 must adhere to enzyme film 15 and provide it with mechanical strength.

Each layer can be formed using dip or spin coating to achieve a thin uniform film. For example, lower protective film 14 can be formed by dripping a thin film of 5% acetyl cellulose (with a solvent composition of 3:1 acetone to cyclohexanone) onto metal electrode 12 and spinning it for five seconds at 2000 rpm. Immobilized enzyme film 15 can be formed in the same way by combining an enzyme with a 0.5% glutaraldehyde solution whose acidity is adjusted by a 0.1M liquid phosphoric acid buffer (Ph 7.0) and spin-coating it. Upper protective film 16 can be formed by dip-coating at 1 cm/sec a thin film of 2.5% acetyl cellulose (with a solvent composition of 1:1 acetone to ethanol).

In the present embodiment, the generally planar hydrogen peroxide electrode which serves as base electrode 10 may, for example, be formed on the surface of an insulating film 11, which consists of a ceramic or resin film. Metal electrode 12 may be at the user's discretion, formed as a thin film of platinum, gold or silver. In immobilized enzyme films 13, enzyme film 15 is a film of GOD or LOD which is immobilized by forming a bridge over it. The function of the upper protective film 16 is enhanced if it is covered by a thin film 17 of nylon lattice or polycarbonate.

Figure 6:
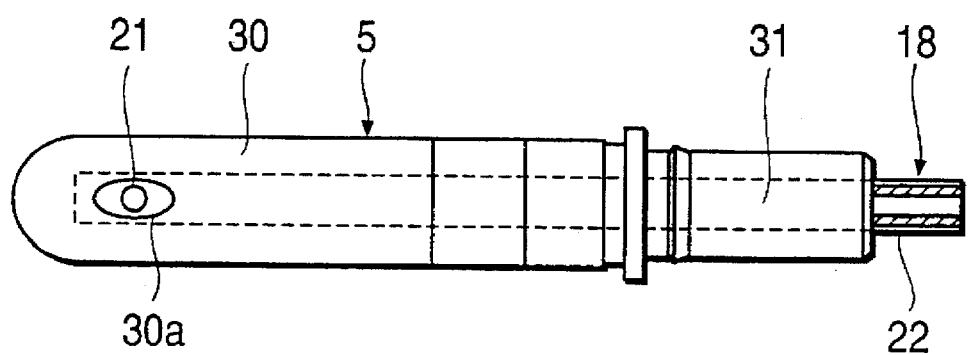
FIG. 6 is an overhead view of the sensor holder.
Figure 8:
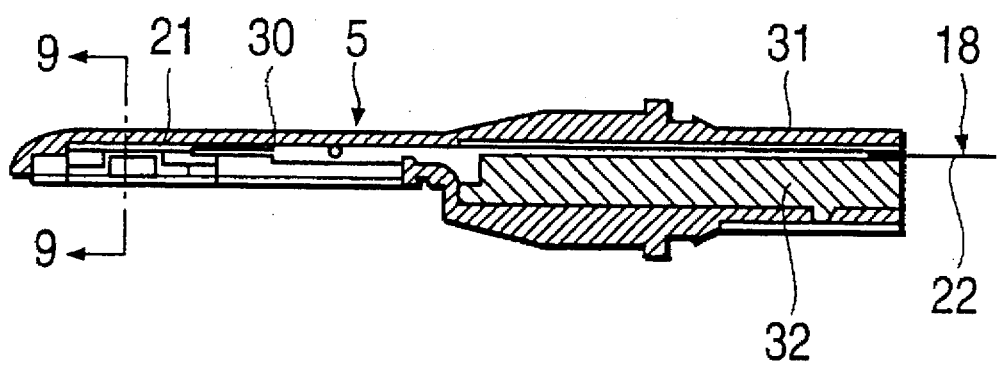
FIG. 8 is a cross section of the sensor holder in FIG. 7.

A sample configuration for sensor holder 5, which contains the enzyme sensor 18 described above, is shown in FIGS. 6 (overhead view), 7 (lateral view), 8 (vertical cross section) and 9 (cross section taken along line A—A in FIG. 8). With the exception of reactive portion 21 and connector 22, the enzyme sensor 18 is enclosed in sensor holder 5.

Since enzyme sensor 18 is entirely enclosed in holder 5, there is no need to install an additional protective film after changing sensor 18 or before starting a measurement. Furthermore, when enzyme sensor 18 is replaced, enzyme sensor holder 5 can be replaced along with it. This insures that the replacement procedure will not affect the contact between the electrode surface and the enzyme film, and that the contact will remain constant. Connector 22 on sensor 18 protrudes from holder 5. When enzyme sensor holder 5 is inserted into measurement main body 2, connector 22 is connected to the circuit in main body 2. Thus eliminating a need for a lead wire and making it easier to replace the sensor 18. In addition, reliability of the connection is also enhanced.

Figure 9:
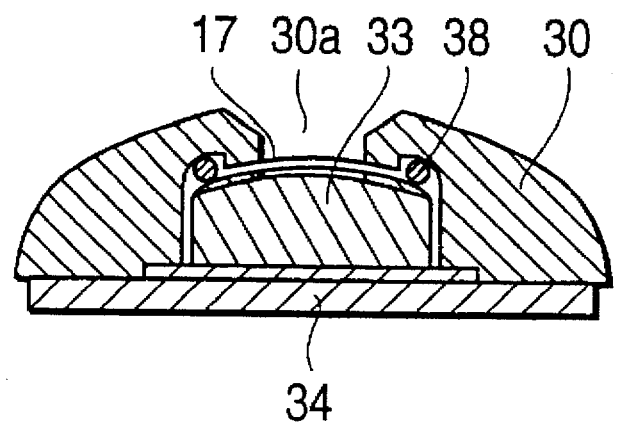
FIG. 9 is a cross section of the sensor holder in FIG. 8 taken along line A—A.

In FIG. 8, enzyme sensor holder 5 comprises a segment 30, which has an opening 30a (See FIG. 6) corresponding to reactive portion 21 of sensor 18. Segment 31, on which an O ring (not pictured) is installed to prevent water or foreign material from entering the measurement main body 2, is screwed onto segment 30. Segment 32 positions and anchors connector 22 on sensor 18 with respect to segment As shown in FIG. 9, segment 33, which protrudes to position reactive segment 34, which anchors the area about reactive portion 21 of sensor 18 with respect to segment 33. If, for example, we weld segments 30 through 34 of the sensor holder, we can effectively prevent the sample, water, or other foreign substances from entering sensor holder 5.

In FIG. 9, protective film 17 in enzyme sensor 18 is kept in contact with the sensor by the O ring 38. When protective film 17 has been mounted in segment 30 of the sensor holder, enzyme sensor 18 and segment 33 of the sensor holder are successively inserted. They are held in place by segment 34 of the sensor holder 5, and protective film 17 is held in contact with reactive portion 21 of enzyme sensor 18. The O ring 38 prevents portions of the sample, cleaning water, or other foreign substances from entering the interior of enzyme sensor holder 5 through opening 30a in segment 30 of the sensor holder 5.

The opening 30a in segment 30 of the sensor holder 5 is bowl-shaped (see FIG. 9). It is elliptical, with its longer axis parallel to the length of enzyme sensor holder 5 and its shorter axis perpendicular (see FIG. 6). This design enables the liquid medium to easily enter opening 30a when cover 3 is attached to measurement main body 2, i.e., when enzyme sensor 18 is immersed in the medium inside cover 3. While at the same time, the elliptical opening makes it unlikely for air bubbles to become trapped there. The end of enzyme sensor holder 5 is smoothly tapered (i.e., curved) so that it can easily be inserted into cover 3.

Figure 7:
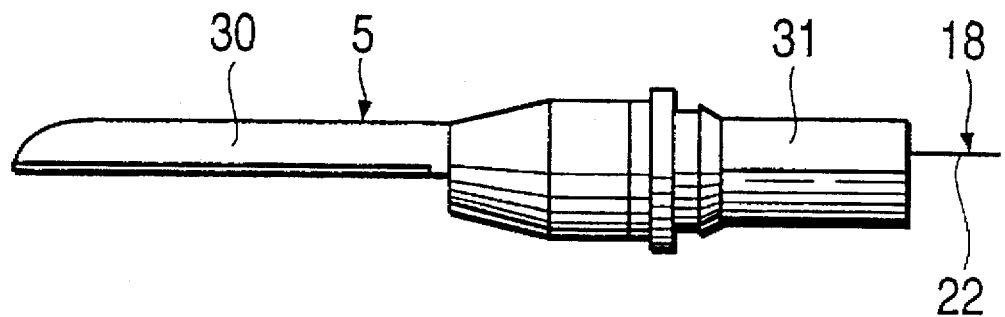
FIG. 7 is a lateral view of the sensor holder in FIG. 6.

In FIG. 9, segment 30 of the sensor holder 5 has a hemispherical cross section of which the missing central portion forms opening 30a. Segment 34 of the sensor holder 5 can be flat, or it can have a cross section which is less curved than segment 30. Then even if the sample is poured directly onto reactive portion 21 of sensor 18, it will not diffuse into the region surrounding opening 30a. This allows a wide variety of methods to be used to supply the sample to opening 30a, thus making the sensor easier to use. As can be seen in FIGS. 7 and 8, the rear portion of the enzyme sensor holder 5 (segments 31 and 32) is asymmetrical. This prevents enzyme sensor holder 5 from being inserted the wrong way into the measurement main body 2.

Figure 10:
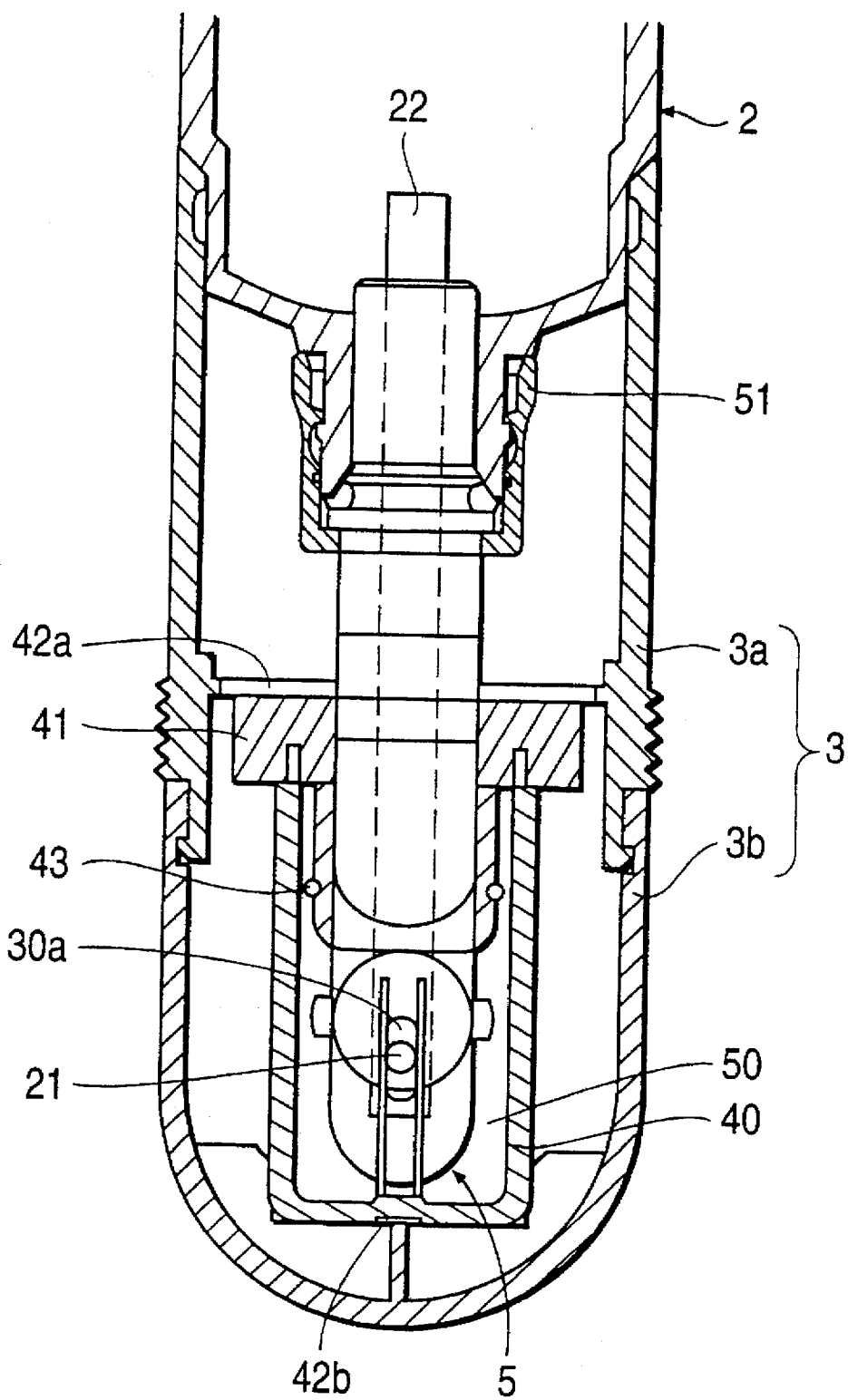
FIG. 10 is a vertical cross section showing the end portion of the measurement device and the cover with the sensor holder installed.

FIG. 10 shows a sample configuration for cover 3 and the end portion of measurement main body 2 (with enzyme sensor holder 5 inside it). Cover 3, which contains a chamber 50 formed by a cartridge 40 filled with a liquid medium, can be attached to or removed from the measurement main body 2. Cover 3 includes a base segment 3a and top segment 3b. Base segment 3a can be attached to or removed from the measurement main body 2. Top segment 3b can be attached to or removed from the base segment 3a. The liquid medium in cover 3 is contained in a chamber 50 formed by cartridge 40 and packing 41. Cartridge 40 and packing 41 are held between and anchored in place by a stop 42a on the base segment 3a and stop 42b on the top segment 3b of the cover 3. Packing 41 and stops 42a and 42b effectively prevent the liquid medium from leaking out and enhance the watertightness of the sensor. When cover 3 is put on or taken off the measurement main body 2, i.e., when enzyme sensor holder 5 is inserted into or removed from cover 3, cartridge 40, packing 41 and stoppers 42a and 42b maintain enzyme sensor holder 5 in its correct position at all times. Since base segment 3a and top segment 3b of the cover 3 are removable, cartridge 40 can easily be washed and the liquid medium in the cover 3 can easily be topped up or changed.

In the center of packing 41 is a declivity of a shape which approximates the end of sensor holder 5, into which enzyme sensor holder 5 is inserted. A slit which is continuous with this declivity opens or closes depending on the presence of sensor holder 5. Ideally, a contracting ring 43 should be installed to assist in the opening and shutting of the slit. This will improve the seal when the slit is closed. This design will not only prevent dust and other foreign substances from contaminating the liquid medium, but will also effectively prevent the liquid medium from leaking out of the sensor holder 5.

The portion of packing 41 with the slit may be formed after packing 41 is manufactured or may be formed as two pieces which can be put together and pressed into cover 3. The portion of packing 41 which is not pressed into the cover 3 is a free piece. The slit may be formed in this free piece.

Anchor 51 is provided on the end portion of the measurement main body 2 so that enzyme sensor holder 5 will not easily separate from the main body 2 when the cover 3 is removed. Enzyme sensor 18, which is inside sensor holder 5, normally remains stable in its measurement state, even when not performing a measurement. Enzyme sensor holder 5 is securely immobilized in measurement main body 2 by anchor 51. The holder 5 will not be dislodged from the main body 2 when it is shaken lightly or washed, though it can be removed when enzyme sensor 18 needs to be replaced.

Figure 11:
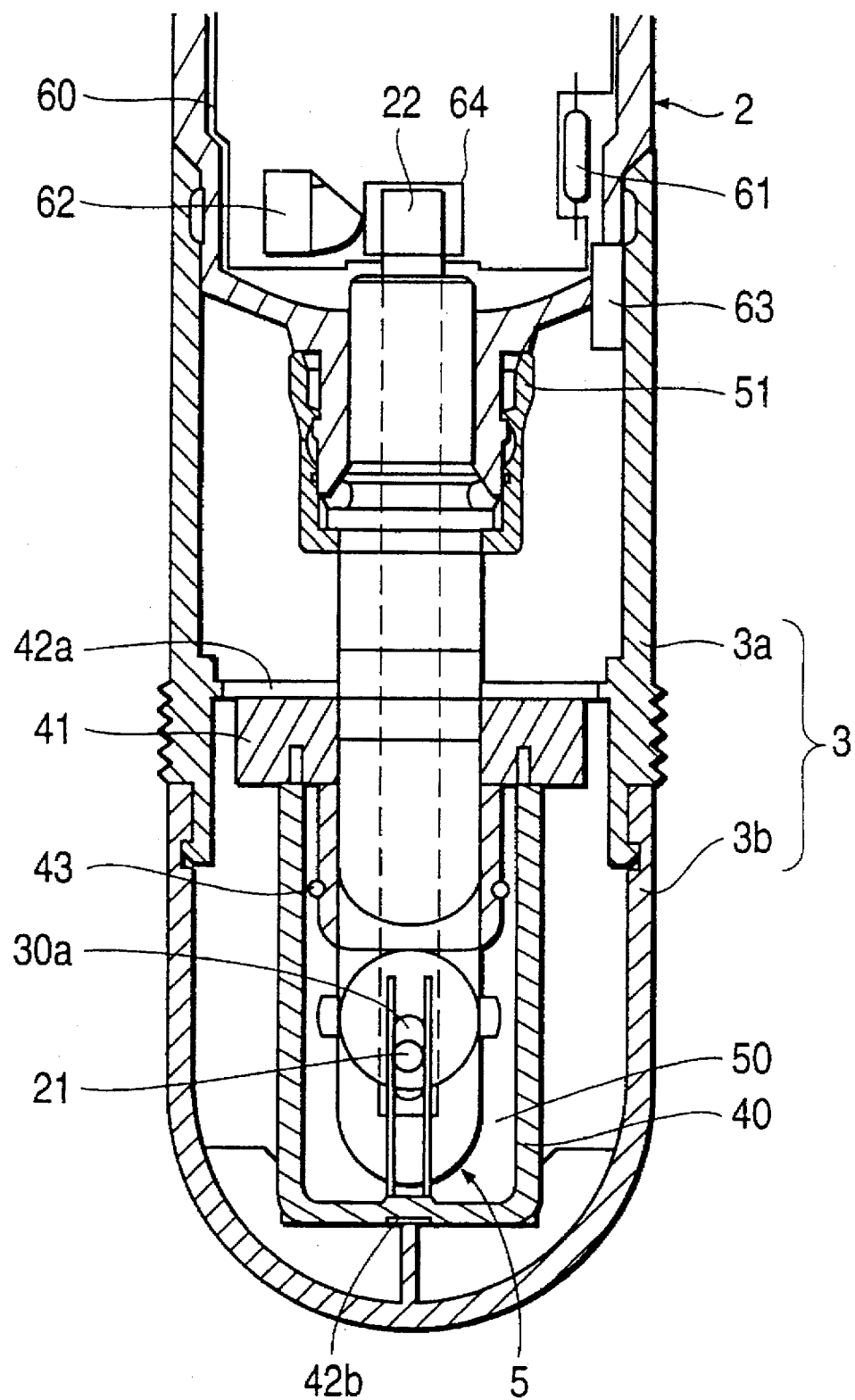
FIG. 11 is a vertical cross section of another ideal embodiment of this invention showing the end of the measurement device and the cover with the sensor holder installed.

FIG. 11 shows another embodiment of the present invention which includes a device to detect whether enzyme sensor holder 5 (and with it, enzyme sensor 18) is installed in the measurement main body 2 and whether cover 3 is on the main body 2. With the exception of this detector, the configuration of this device is identical to that shown in FIG. 10. Identical components have been given the same numbers as in FIG. 10, and therefore omitting any further discussion of them. In this embodiment, measurement circuit board 60 extends all the way to the base end of sensor holder 5. Lead relay 61 is mounted on the portion of the circuit board 60 where measurement main body 2 engages with cover 3. Microswitch 62 is mounted on the corresponding portion of the sensor holder 5. Connector 64, which is electrically connected to enzyme sensor 18, is mounted on the portion of the board which faces connector 22 on sensor 18, which protrudes from sensor holder 5. Magnet 63 is mounted on the corresponding portion of cover 3.

With this type of detector, the action of magnet 63 will cause lead relay 61 to turn on when cover 3 is installed on the measurement main body 2. This way the fact that cover 3 is on the device 1 is detected. If this arrangement is used, removing cover 3 will automatically cause the device 1 to be initialized for measurement. This will obviate the need to provide a start switch on measurement main body 2. When the enzyme sensor holder 5 is inserted into the measurement main body 2, a connector 22 on the enzyme sensor 18 is connected to the connector 64 on the circuit board 60 and the microswitch 62 turns on. This way the device 1 detects that the enzyme sensor holder 5 has been installed. If cover 3 is placed when enzyme sensor holder 5 is not inserted, that is, when enzyme sensor 18 is not immersed into the liquid medium in cover 3, this will also be detected.

This detector will enable the user to detect reliably every instance in which the cover 3 or the enzyme sensor holder 5 is not installed. To inform the user based on a signal from the detector that the cover 3 or the enzyme sensor holder 5 is or is not present, a message can be displayed on the display 6 of the measurement main body 2 or a buzzer could sound.

The following explains the operation of the measurement device 1 as described herein. When a measurement is to be made, the cover 3 is first removed from the measurement main body 2. A visual display 6 or buzzer informs the user that measurement can now proceed. Opening 30a in enzyme sensor holder 5 is immersed in a container which has been filled with a sample, or the sample may be poured continuously onto opening 30a. The display 6 or buzzer indicates that measurement has been completed and the operation is finished. The measurement result appears on the display 6. Opening 30a in sensor holder 5, that is, the environment of reactive portion 21 on enzyme sensor 18, is washed with water or some other cleaning agent and the cover 3 is placed back on the measurement main body 2.

What is claimed is:

1. A portable biochemical device, comprising:

a measurement main body including a measurement circuit and a power supply;

an enzyme sensor holder projecting from said measurement main body and including an enzyme sensor thereon which is connected electrically to the measurement main body; and a cover covering the enzyme sensor holder and the enzyme sensor, wherein the cover contains a cartridge filled with a medium to maintain moisture of the enzyme sensor.

2. A portable biochemical measurement device according to claim 1, wherein the cover is removable from the measurement main body.

3. A portable biochemical measurement device according to claim 1, wherein the cover is comprised of a top and a base segment, the top segment being removable from the base segment.

4. A portable biochemical measurement device according to claim 3, wherein the top segment comprises a removable cartridge and a removable packing.

5. A portable biochemical measurement device according to claim 4, wherein when the top segment is engaged with the base segment, the cartridge and the packing are fixed in a correct position inside the cover.

6. A portable biochemical measurement device according to claim 4, wherein the packing contains a slit to insert the enzyme sensor holder, thereby allowing the enzyme sensor to become immersed in the medium.

7. A portable biochemical measurement device according to claim 1, wherein the enzyme sensor is a disposable sensor.

8. A portable biochemical measurement device according to claim 7, wherein the enzyme sensor consists of an immobilized enzyme film formed on a hydrogen peroxide electrode, wherein the electrode is formed on an insulated substrate.

9. A portable biochemical measurement device according to claim 7, wherein the enzyme sensor is covered by a protective film.

10. A portable biochemical measurement device according to claim 9, wherein the protective film is fastened by an O ring installed in the sensor holder, said enzyme sensor is fitted in said enzyme sensor holder such that the protective film adheres to the enzyme sensor, making interior of the enzyme sensor watertight.

11. A portable biochemical measurement device according to claim 1, further comprising a detector to detect if the cover is installed in the measurement main body.

12. A portable biochemical measurement device according to claim 1, further comprising a detector to detect if the enzyme sensor holder is installed in the measurement main body.

* * * * *